(12) United States Patent
Xu et al.

(10) Patent No.: US 11,020,092 B2
(45) Date of Patent: Jun. 1, 2021

(54) MULTI-SITE CONCURRENT ULTRASOUND BLOOD FLOW VELOCITY MEASUREMENT FOR CONTINUOUS HEMODYNAMIC MANAGEMENT

(71) Applicant: KONINKLIJKE PHILIPS N.V., Eindhoven (NL)

(72) Inventors: Minnan Xu, Cambridge, MA (US); Balasundar Iyyavu Raju, North Andover, MA (US); Ajay Anand, Fishkill, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 321 days.

(21) Appl. No.: 16/061,455

(22) PCT Filed: Dec. 22, 2016

(86) PCT No.: PCT/EP2016/082395
§ 371 (c)(1),
(2) Date: Jun. 12, 2018

(87) PCT Pub. No.: WO2017/109080
PCT Pub. Date: Jun. 29, 2017

(65) Prior Publication Data
US 2020/0261059 A1    Aug. 20, 2020

Related U.S. Application Data

(60) Provisional application No. 62/270,877, filed on Dec. 22, 2015.

(51) Int. Cl.
*A61B 8/08*    (2006.01)
*A61B 8/06*    (2006.01)
*A61B 8/00*    (2006.01)

(52) U.S. Cl.
CPC .............. *A61B 8/488* (2013.01); *A61B 8/06* (2013.01); *A61B 8/4477* (2013.01)

(58) Field of Classification Search
CPC ......... A61B 8/488; A61B 8/06; A61B 8/4477; A61B 8/42; A61B 8/4236; A61B 8/0891;
(Continued)

(56) References Cited

U.S. PATENT DOCUMENTS 7,621,876 B2 * 11/2009 Hoctor ............... A61B 5/02125
600/437
7,857,763 B2    12/2010 Tai
(Continued)

FOREIGN PATENT DOCUMENTS

JP    2004290408 A    10/2004
WO    99008597    2/1999
(Continued)

OTHER PUBLICATIONS

Marik, et al., "The Use of Bioreactance and Carotid Doppler to Determine Volume Responsiveness and Blood Flow Redistribution Following Passive Leg Raising in Hemodynamically Unstable Patients"; CHEST, Original Research, 2014.

*Primary Examiner* — Serkan Akar
*Assistant Examiner* — Richmond J Van Winter

(57) ABSTRACT

A Doppler ultrasound instrument (10) includes ultrasound pulse control and data acquisition electronics (12, 24, 26) for acquiring Doppler ultrasound data, an N-channel connector port (14) for simultaneously operatively connecting up to N ultrasound transducer patches (16) where N is an integer equal to or greater than two, and an electronic processor (30) programmed to concurrently determine up to N blood flow velocities corresponding to up to N patches operatively connected to the N channel connector port. The blood flow velocity for each patch may be determined by: determining transducer blood flow velocities for ultrasound transducers (Continued)

(60) of a transducer array of the patch; and determining the blood flow velocity for the patch as a highest determined transducer blood flow velocity or as an aggregation of highest determined transducer blood flow velocities.

13 Claims, 5 Drawing Sheets

(58) Field of Classification Search
CPC ... A61B 8/5223; G01P 5/241; G01S 15/8979; G01S 15/8915
See application file for complete search history.

(56) References Cited

U.S. PATENT DOCUMENTS

| | | |
|---|---|---|
| 8,348,847 B2 | 1/2013 | Vezina |
| 2005/0251044 A1 | 11/2005 | Hoctor |
| 2010/0036253 A1* | 2/2010 | Vezina ................. A61B 8/5292 600/453 |
| 2010/0076315 A1 | 3/2010 | Erkamp |
| 2015/0380292 A1 | 12/2015 | Tachioka et al. |
| 2018/0353154 A1* | 12/2018 | Eibl ....................... A61B 8/463 |

FOREIGN PATENT DOCUMENTS

| | | |
|---|---|---|
| WO | 2007040645 | 4/2007 |
| WO | 2015011585 A1 | 1/2015 |

* cited by examiner

MULTI-SITE CONCURRENT ULTRASOUND BLOOD FLOW VELOCITY MEASUREMENT FOR CONTINUOUS HEMODYNAMIC MANAGEMENT

CROSS REFERENCE TO RELATED APPLICATIONS

This application is the U.S. National Phase application under 35 U.S.C. § 371 of International Application No. PCT/EP2016/082395, filed Dec. 22, 2016, published as WO 2017/109080 on Jun. 29, 2017, which claims the benefit of U.S. Provisional Patent Application No. 62/270,877 filed Dec. 22, 2015. These applications are hereby incorporated by reference herein.

FIELD

The following relates generally to the medical ultrasound arts, Doppler ultrasound blood flow testing arts, hemodynamic measurement arts, patient vital sign monitoring arts, and related arts.

BACKGROUND

Doppler ultrasound is a technique used to noninvasively measure blood flow. When ultrasound pulses with a known sonic frequency are applied and reflect from flowing blood, the reflected ultrasonic signals have a sonic frequency shift attributable to the Doppler effect. The magnitude of the Doppler frequency shift is related to the blood flow velocity toward or away from the ultrasound transducer, while the direction of the Doppler frequency shift is related to the direction of blood flow toward or away from the ultrasound transducer. Doppler ultrasound is typically used to detect blood clots or other flow blockages, stenosis, plaque buildup on vessel walls, or other sources of flow reduction. In existing Doppler ultrasound devices for this purpose, a handheld ultrasound transducer is manually pressed against the skin of the patient proximate to a major blood vessel whose blood flow is to be measured. The handheld ultrasound transducer is manually positioned or re-positioned as needed to produce a strong Doppler ultrasound signal due to blood flow. In a common vessel alignment approach, the ultrasound device includes a loudspeaker that outputs audible flow velocity feedback, and the handheld transducer is manually positioned or re-positioned to maximize the volume of this audible feedback. Doppler ultrasound blood flow measurements are typically performed by a specialist known as a diagnostic medical sonographer.

The following discloses a new and improved systems and methods that address the above referenced issues, and others.

SUMMARY

In one disclosed aspect, a Doppler ultrasound device is disclosed. A Doppler ultrasound instrument includes ultrasound pulse control and data acquisition electronics configured to acquire Doppler ultrasound data, an N-channel connector port configured to simultaneously operatively connect up to N ultrasound transducer patches with the ultrasound pulse control and data acquisition electronics (where N is an integer equal to or greater than two), and an electronic processor programmed to concurrently determine up to N blood flow velocities corresponding to up to N ultrasound transducer patches operatively connected to the N channel connector port from Doppler ultrasound data acquired using the respective ultrasound transducer patches. In one approach, the electronic processor of the Doppler ultrasound instrument is programmed to determine the blood flow velocity for each ultrasound transducer patch operatively connected to the N-channel connector port by operations including: determining a transducer blood flow velocity for each ultrasound transducer of an array of ultrasound transducers of the ultrasound transducer patch from Doppler ultrasound data acquired using the ultrasound transducer; and determining the blood flow velocity for the ultrasound transducer patch as a highest determined transducer blood flow velocity of the array of ultrasound transducers or as an aggregation of a set of highest determined transducer blood flow velocities of the array of ultrasound transducers. A blood flow lumen may be determined from a map of the determined transducer blood flow velocities over the array area, and flow mediated dilation (FMD) may be determined based on change in the determined blood flow lumen over time.

In another disclosed aspect, a Doppler ultrasound method comprises: affixing two or more ultrasound transducer patches to different locations on a hemodynamic measurement subject; concurrently acquiring Doppler ultrasound data using the two or more ultrasound transducer patches affixed to the different locations on the hemodynamic measurement subject; and determining a blood flow velocity for each location using the Doppler ultrasound data acquired using the ultrasound transducer patch affixed to the location.

In another disclosed aspect, a Doppler ultrasound method comprises: affixing an ultrasound transducer patch including an array of ultrasound transducers to a hemodynamic measurement subject; acquiring Doppler ultrasound data using each transducer of the array of ultrasound transducers of the affixed ultrasound transducer patch; determining a transducer blood flow velocity for each ultrasound transducer of the array of ultrasound transducers of the affixed ultrasound transducer patch using the Doppler ultrasound data acquired by the ultrasound transducer; and determining a blood flow velocity for the ultrasound transducer patch as a highest determined transducer blood flow velocity of the array of ultrasound transducers or as an aggregation of a set of highest determined transducer blood flow velocities of the array of ultrasound transducers.

One advantage resides in facilitating comparative Doppler ultrasound blood flow assessment of different major blood vessels.

Another advantage resides in providing Doppler ultrasound blood flow assessment devices with relaxed requirements for ultrasound transducer placement.

Another advantage resides in providing Doppler ultrasound blood flow assessment providing spatial information without generating an ultrasound image.

Another advantage resides in facilitating circulatory system-level assessments by Doppler ultrasound blood flow measurements.

Another advantage resides in measuring hemodynamic response to a single applied stimuli, such as a single fluid challenge, in several major blood vessels.

Another advantage resides in providing for Doppler ultrasound blood flow assessment as an automatically monitored patient vital sign.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
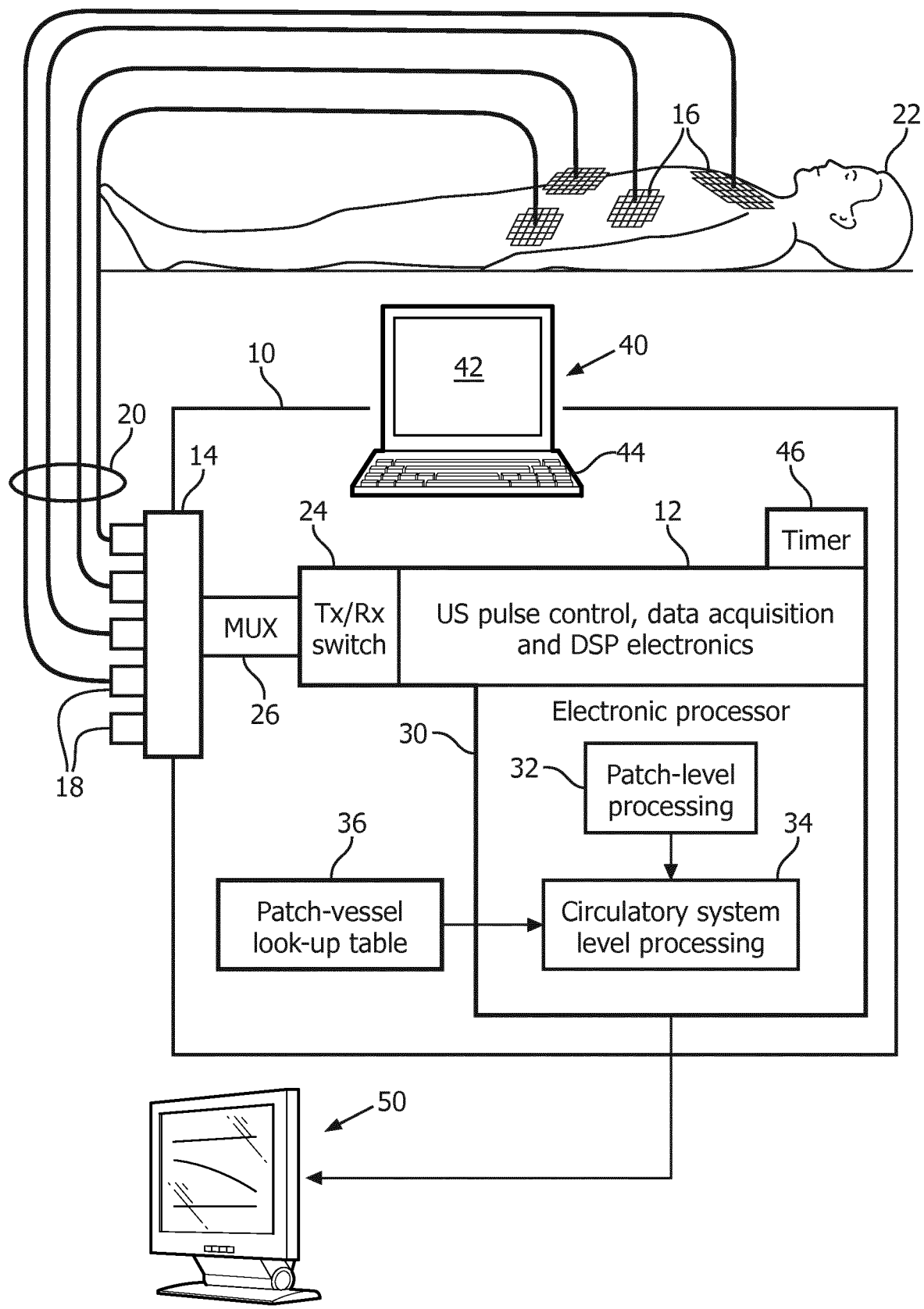
FIG. 1 diagrammatically shows a Doppler ultrasound device for measuring hemodynamic blood flow as disclosed herein.

Doppler ultrasound embodiments disclosed herein overcome certain deficiencies recognized herein of existing Doppler ultrasound devices, and provide additional capabilities that go beyond those provided by existing Doppler ultrasound devices.

A disadvantage of existing Doppler ultrasound devices is that proper positioning of the handheld ultrasound transducer probe is difficult, even with audible flow velocity feedback. If the sonographer measures blood flow in an initial blood vessel, then moves the probe to a different blood vessel and subsequently returns to the initial blood vessel for a re-measurement, the probe is prone to be positioned differently for the re-measurement as compared with the initial measurement, leading to degraded reproducibility. Such difficulties contribute to conventionally employing a specially trained sonographer to perform a Doppler ultrasound examination.

Another disadvantage with existing Doppler ultrasound is that it is difficult to accurately measure hemodynamic response of two or more different blood vessels to a stimulus, such as a fluid challenge. One way to do this is to repeat the stimulus for each blood vessel, but this is time consuming and can lead to memory effects from previously applied stimuli. Another approach is to perform a single stimulus, and then rapidly move the ultrasound transducer probe from one blood vessel to the next to acquire Doppler ultrasound data for the various blood vessels. This latter approach requires the sonographer to act quickly to examine each blood vessel in turn within the typically short time window over which the stimulus response can be assessed, and limits the achievable temporal resolution and may lead to incomplete data sets for the various measured blood vessels.

In improvements disclosed herein, the Doppler ultrasound device includes an N-channel connector port configured to simultaneously operatively connect up to N ultrasound transducer patches with ultrasound pulse control and data acquisition electronics (where N is an integer equal to or greater than two). The Doppler ultrasound device further includes an electronic processor which may be separate from or integrated with the ultrasound pulse control and data acquisition electronics. The electronic processor is programmed to concurrently determine up to N blood flows velocities corresponding to up to N ultrasound transducer patches operatively connected to the N-channel connector port. Each blood flow velocity is determined from Doppler ultrasound data acquired using the respective ultrasound transducer patch. The ultrasound transducer patches are preferably configured to be affixed to the subject, for example using an adhesive (e.g. gel) to adhere each transducer patch to skin of the subject, or using a wrap (e.g. gauze) to tie the transducer patch to an arm or leg or neck of the subject, or so forth.

In some embodiments, each ultrasound transducer patch includes an array of transducers, and the blood flow velocity for the patch is determined as the highest transducer blood flow velocity for any transducer of the array, or as an aggregation (e.g. average) of the highest several transducer blood flow velocities. This approach relaxes the precision with which the ultrasound transducer patch must be placed, since it is only needed that there be some overlap between the transducer array area and the blood vessel to be measured. This approach also enables new capabilities, such as assessing the blood vessel lumen in a straightforward fashion using a map of transducer blood vessel velocities over the array. Blood vessel lumen can be measured over time, enabling assessment of flow mediated dilation (FMD) based on change in the determined blood flow lumen over time.

The ability to concurrently measure blood flow velocities at up to N different locations using up to N ultrasound transducer patches also enables new capabilities. For example, hemodynamic response to a stimulus, such as a fluid challenge, can be concurrently assessed for up to N different blood vessels using a single instance of the stimulus. In the case of a fluid challenge, for example, this enables rapid assessment of preferential diversion of fluid to the brain via the carotid arteries, which can be an indicator of certain hemodynamic disease states. In another enabled capability, blood flow in a trunk blood vessel, such as the aorta, can be indirectly assessed by measuring blood flow velocities in the several branching blood vessels that connect with the trunk blood vessel and taking into account the various branching blood vessel lumens. The advantage here is that branching blood vessels might be easier to access than the aorta.

The ability to position and affix one or more ultrasound transducer patches with rough precision (due to the larger area of the transducer array which calls for less precise alignment of the patch placement with the target blood vessel) also facilitates the use of Doppler ultrasound for routine patient monitoring. Such monitoring is contemplated to be initiated by general-practice medical personnel (e.g. a nurse) rather than by a specially trained sonographer, and can be used to automatically monitor blood flow velocities on a periodic basis (e.g. every ten to fifteen minutes). This enables Doppler ultrasound blood flow velocities (or blood vessel lumen, or another hemodynamic parameter measureable by the disclosed Doppler ultrasound) to be treated as a vital sign that is measured as part of routine patient monitoring.

With reference now to FIG. 1, a Doppler ultrasound instrument 10 includes ultrasound pulse control and data acquisition electronics 12 configured to acquire Doppler ultrasound data. An N-channel connector port 14 is configured to simultaneously operatively connect up to N ultrasound transducer patches 16 with the ultrasound pulse control and data acquisition electronics 12 (where N is an integer equal to or greater than two). In the illustrative embodiment, the N-channel connector port 14 includes N connectors 18 (namely N=5 connectors 18 in the illustrated example of FIG. 1, but more generally N is an integer that can be any value of one or higher, and more preferably N is an integer that is greater than or equal to two in order to support simultaneous connection of multiple ultrasound transducer patches 16). Each ultrasound transducer patch 16 is physically separate from the other patches (although terminal connection to a common electrical cable pigtail is contemplated if the leads from the pigtail to the individual patches 16 are long enough to enable independent patch placement), and accordingly each ultrasound transducer patch 16 can be independently affixed to a different location so as to use the different patches 16 to measure different major blood vessels. For example, in illustrative FIG. 1 one patch 16 is affixed in the neck region, another patch 16 is affixed in the upper torso region, and two further patches 16 are affixed to different lower regions. Each illustrated connector 18 of the N-channel connector port 14 is configured to connect with a single ultrasound transducer patch 16, for example by way of an electrical cable 20 of the patch 16 that has a distal end with a suitable mating electrical connector that mates with the electrical connector 18 of the N-channel connector port 14. Not all of the N connectors 18 are necessarily used at any given time—for example, in illustrative FIG. 1 only four ultrasound transducer patches 16 are connected with four of the N=5 connectors 18. So that one connector 18 is not currently in use. In another contemplated embodiment, the N-channel connector port may include one connector that is configured to connect with an N-to-1 pigtail connector of a bundle of N ultrasound transducer patches.

Each ultrasound transducer patch 16 that is in use is affixed to a hemodynamic measurement subject 22, for example by a gel or other adhesive. Alternatively, the transducer patches 16 may be affixed to the subject 22 by an encircling strap, gauze wrap, or so forth that physically ties the transducer patch to the desired location of the subject 22. Other affixation mechanisms are also contemplated.

The ultrasound pulse control and data acquisition electronics 12 include various components (details not shown), such as ultrasound beam forming control electronics for generating electrical pulses with designed amplitude, frequency, duration and/or other characteristics that when applied to an ultrasound transducer (e.g., piezoelectric transducer or capacitive transducer) generate ultrasound beam pulses typically focused at a target depth, operating a transmit/receive (Tx/Rx) switch 24 to synchronize ultrasound pulse emissions with reflected ultrasound measurements received using the transducer, electronic filter(s) and/or amplifier(s) for filtering and/or amplifying the received ultrasound measurements, analog-to-digital conversion (ADC) circuitry for converting the filtered and/or amplified ultrasound reflection measurements to digital ultrasound data, and post-acquisition digital signal processing (DSP) for processing the digitized ultrasound data to produce clinically useful output such as brightness mode (B-mode) images, Doppler ultrasound spectral and/or flow velocity data, or so forth.

The N-channel connector port 14 is configured to simultaneously operatively connect up to N ultrasound transducer patches 16 with the ultrasound pulse control and data acquisition electronics 12. In the illustrative embodiment, this is accomplished by way of the Tx/Rx switch 24 and a multiplexor (MUX) 26 that is switchable to sequentially drive each transducer patch connector 18 in turn at a high switching rate to acquire Doppler ultrasound data from two or more (e.g., illustrative four) simultaneously operatively connected ultrasound transducer patches 16 in near-real time. In another contemplated embodiment (not shown), the MUX 26 is omitted in favor of multi-channel electronics that independently drive each transducer patch connector 18 so as to enable acquiring Doppler ultrasound data from two or more connected transducer patches 16.

The ultrasound pulse control and data acquisition electronics 12 are configured to perform Doppler ultrasound blood flow measurements. In a typical approach, ultrasound pulses are applied to an ultrasound transducer (e.g. piezoelectric or capacitive transducer) of the ultrasound transducer patch 16 with a known sonic frequency. The transducer coverts the electrical pulses to sonic pulses with the sonic frequency, and after switching the Tx/Rx switch 24 the reflected ultrasound pulses are detected. The frequency shift (if any) observed in the reflected ultrasound signal is attributed to blood flow altering the reflected sonic frequency by way of the Doppler effect. Blood flow direction toward or away from the transducer is determinable from the polarity of the Doppler frequency shift, while the magnitude of the Doppler frequency shift is a measure of the flow velocity component along the ultrasound beam direction. Blood flow turbulence can be quantified by statistical measures such as variance of the reflected sonic frequency. Depth profiling can be performed by scanning the beam focus of the formed ultrasound beam.

Optionally, Doppler blood flow imaging can be performed by laterally scanning the focused ultrasound beam, and the image can be color coded to indicate blood flow direction, velocity, turbulence, or other flow information. In general, Doppler ultrasound data can be acquired with various spatial focusing or scanning and processed to produce various types of Doppler ultrasound clinical output, e.g. color Doppler ultrasound, pulsed wave (PW) Doppler ultrasound, continuous wave (CW) Doppler ultrasound, power Doppler ultrasound, various combinations thereof, or so forth.

To process the Doppler ultrasound data to extract clinically useful information such as blood flow velocity, direction, or the like, and optionally also circulatory system-level information, the illustrative Doppler ultrasound instrument 10 further includes an electronic processor 30 that is programmed to perform Doppler ultrasound data processing such as concurrently determining up to N blood flows velocities corresponding to the up to N ultrasound transducer patches 16 operatively connected to the N channel connector port 14. The blood flow velocities are determined from Doppler ultrasound data acquired using the respective ultrasound transducer patches 16. It will be appreciated that the electronic processor 30 may be separate from or integrated with the ultrasound pulse control and data acquisition electronics 12—for example, the components 12, 30 may be constructed on a common motherboard or hybrid circuit board, and/or a single microprocessor may be programmed to perform various functionality of both components 12, 30, or so forth. Moreover, although not indicated in FIG. 1 it will be appreciated that operational communication between the components 12, 30 may be performed—for example, the electronic processor 30 may send configuration data to the ultrasound pulse control and data acquisition electronics 12 to configure pulse parameters (e.g. frequency, duration, waveform) and cause the ultrasound pulse control and data acquisition electronics 12 to execute a Doppler ultrasound data acquisition sequence, and the resulting data are transferred from the ultrasound pulse control and data acquisition electronics 12 to the electronic processor 30 for post-acquisition processing.

As diagrammatically shown in FIG. 1, processing suitably performed by the electronic processor 30 includes performing patch-level processing 32 to extract information for each ultrasound transducer patch 16 such as a blood flow velocity, blood vessel lumen, spectral Doppler information quantifying the flow profile, quantitative Doppler parameters such as Peak Systolic Velocity (PSV), End Diastolic Velocity (EDV), Resistance Index (RI) and Pulsatility Index computed from the Doppler ultrasound data, or so forth. Volumetric flow rate can be computed using a-priori information about the diameter of the vessel or real-time blood flow lumen measurement obtained from the Doppler ultrasound as disclosed herein. Such clinical data generated from the Doppler ultrasound data acquired by a single ultrasound transducer patch is expected to correspond to a single blood vessel (or, to a group of closely spaced blood vessels in the aggregate). Optionally, further circulatory system-level processing 34 is performed to combine clinical information generated for individual blood vessels by the various patches 16 to generate hemodynamic information for a trunk blood vessel, to provide comparative hemodynamic information comparing blood flow in different measured blood vessels, or so forth. To perform the circulatory system-level processing 34, a patch-vessel look-up table 36 may be provided to identify the major blood vessel that each ultrasound transducer patch 16 is positioned to measure by Doppler ultrasound. Because this information depends upon the manual placement of the various patches 16 on the hemodynamic measurement subject 22, the vessel identifications stored in the look-up table 36 are typically entered by the diagnostic medical sonographer, nurse, or other medical person setting up the Doppler ultrasound.

As further illustrated in FIG. 1, the Doppler ultrasound instrument 10 further includes user interface hardware 40, typically comprising a display component 42 and a keyboard 44, mouse, or other user input device(s). The user interface 40 may, for example, display a whole-body diagram representing the hemodynamic measurement subject 22 on the display component 42, and the user can click on portions of the diagram to indicate where each ultrasound transducer patch 16 is placed—the most closely proximate major blood vessel is then assigned to the corresponding patch in the look-up table 36. Other data entry approaches can be used, such as having the user manually type in (or select from a drop-down list) the name of each blood vessel. Various Doppler ultrasound clinical results may be displayed on the display component 42, such as a color Doppler image, or a list of blood flow velocities measured by the various patches 16, or so forth.

In some embodiments, the Doppler ultrasound instrument 10 is designed to perform automated monitoring of the hemodynamic measurement subject 22. For example, the electronic processor 30 of the Doppler ultrasound instrument may be programmed to automatically repeat, at a programmed automatic repetition time interval, the concurrent determination of up to N blood flows velocities corresponding to up to N ultrasound transducer patches 16 operatively connected to the N-channel connector port 14 from Doppler ultrasound data acquired using the respective ultrasound transducer patches 16. To this end, a clock or timer 46 may be included in the Doppler ultrasound instrument 10 to trigger these automatic repetitions; alternatively, an external trigger input may be applied to the Doppler ultrasound instrument 10 for this purpose. With such automated measurement repetition, the Doppler ultrasound instrument 10 can be viewed as a vital sign monitor that provides hemodynamic information, such as blood flow velocities in one or more major blood vessels. This hemodynamic vital sign data may be transferred to a patient monitor 50 via Ethernet, WiFi, or another communication pathway and displayed on the patient monitor 50 as an illustrative trend line, and/or as a numeric display, or so forth. Advantageously, the Doppler ultrasound flow measurement vital sign data can be integrated with other vital signs such as pulse oximetry, electrocardiography (ECG), capnography, or so forth to output an assessment of a patient's fluid status.

Simultaneous monitoring of blood flow in different major blood vessels in this way provides a wealth of clinical information. For example, the carotid arteries supply most of the blood to the brain. Therefore, by monitoring blood flow in one or both carotid arteries, an assessment of cerebral perfusion can be made. As another example, slow blood flow to the kidney may result in kidney failure—thus, monitoring of blood flow in the renal artery supplying blood to the kidney provides a noninvasive and continuous (or periodic) measurement of blood flow to the kidneys. These measurements can be done simultaneously for up to N different major blood vessels using the Doppler ultrasound device 10.

Figure 2:
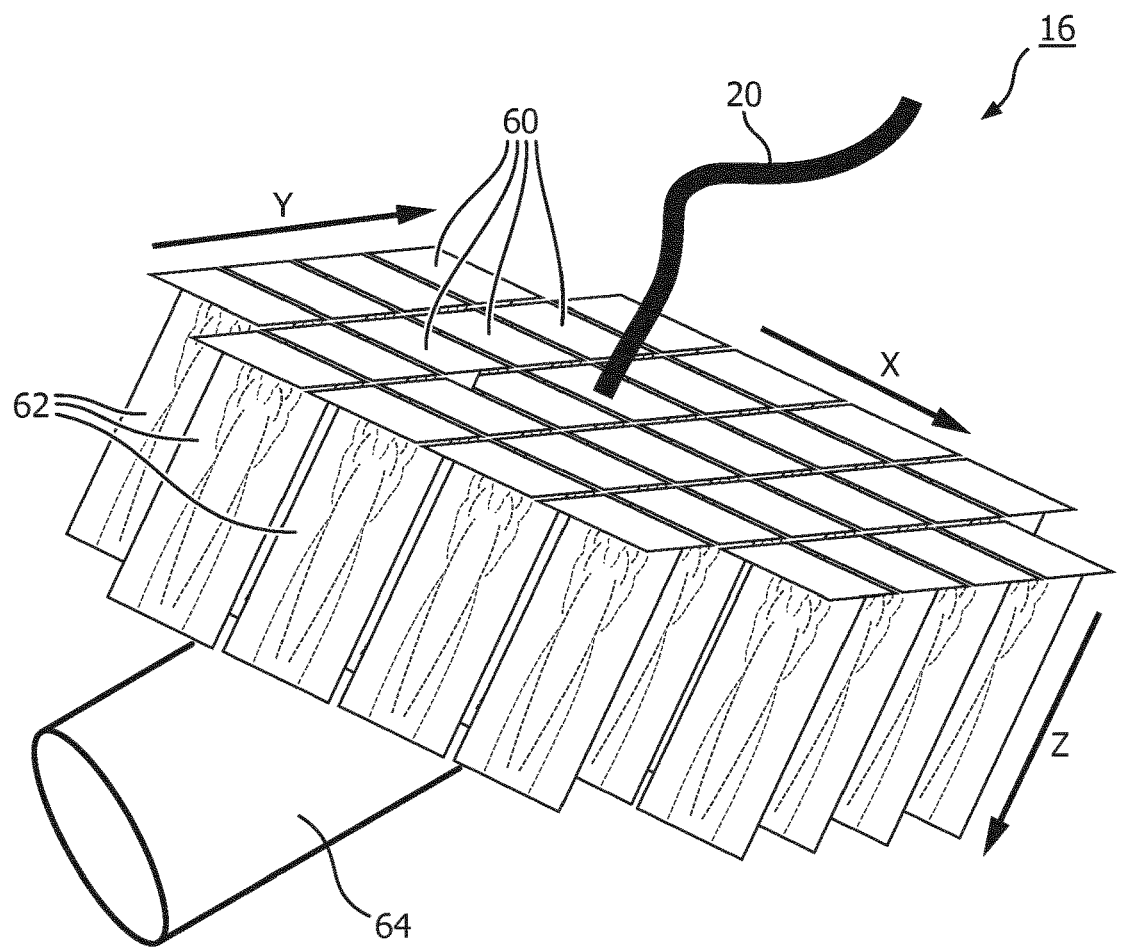
FIG. 2 diagrammatically illustrates one of the ultrasound transducer patches of FIG. 1.

With continuing reference to FIG. 1 and with further reference to FIG. 2, in the illustrative embodiments each ultrasound transducer patch 16 includes an array of ultrasound transducers. In the illustrative example, each transducer 60 operates independently to emit an ultrasound beam 62 and acquire Doppler ultrasound data along a line of sight of the transducer 60. Without loss of generality, for ease of description the ultrasound transducer patch 16 is described with reference to an x-y-z Cartesian coordinate system in which the x-y plane corresponds to the plane of the transducer array and the z-direction is the "depth" direction. Optionally, each individual ultrasound beam 62 is controlled to be focused at a target depth in the z-direction, and a z-direction scan may be implemented. Also diagrammatically shown in FIG. 2 is a target blood vessel 64.

Figure 3:
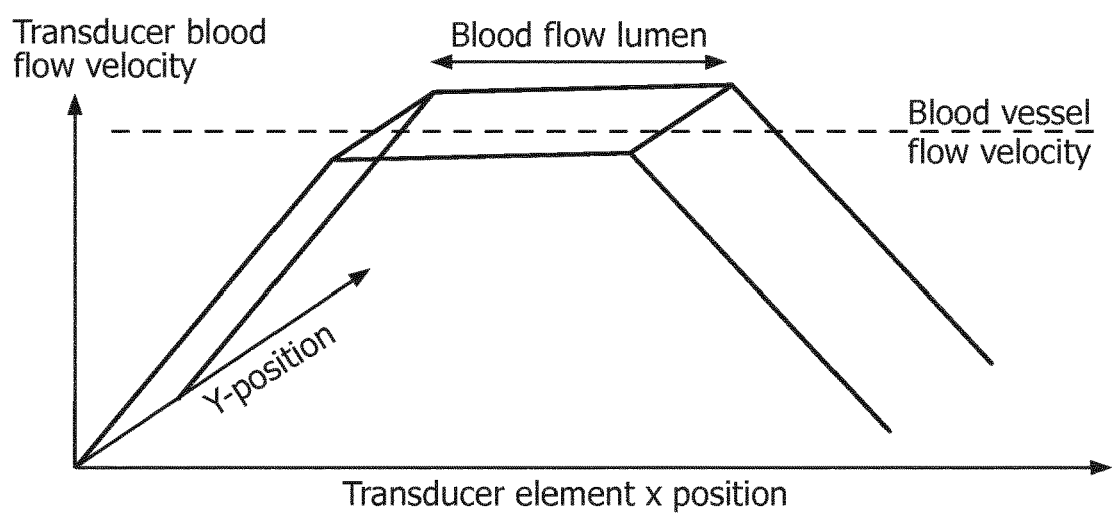
FIG. 3 diagrammatically illustrates determination of hemodynamic parameters such as blood flow velocity and/or effective lumen for a major blood vessel monitored by the ultrasound transducer patch diagrammatically shown in FIG. 2.

With continuing reference to FIG. 2 and with further reference to FIG. 3, in the illustrative ultrasound transducer patch 16 of FIG. 2 the Doppler ultrasound data acquired by each transducer 60 is processed to generate a transducer blood flow velocity acquired by that transducer. As diagrammatically shown in FIG. 3, these transducer blood flow velocities, when plotted as a function of position of the transducer 60, form a velocity map. If the area of the transducer array is larger than the cross-section of the blood flow lumen of the blood vessel 64, then the transducer blood flow velocities for those transducers 60 whose ultrasound beams 62 do not intersect the blood vessel lumen will have low (and possibly near-zero) transducer blood flow velocities since they are probing stationary tissue. On the other hand, the transducer blood flow velocities for those transducers 60 whose ultrasound beams 62 intersect near the center of the blood vessel lumen will have the highest transducer blood flow velocities since they are probing the center of the blood vessel where the flow velocity is expected to be highest. Transducer blood flow velocities for those transducers 60 whose ultrasound beams 62 intersect the periphery of the blood vessel lumen will have intermediate transducer blood flow velocities.

Accordingly, the blood flow velocity for the ultrasound transducer patch 16 is suitably determined as a highest determined transducer blood flow velocity of the array of ultrasound transducers 60. To avoid noise or error due to possible outliers, in a variant embodiment the blood flow velocity for the ultrasound transducer patch 16 is determined as an aggregation of a set of highest determined transducer blood flow velocities of the array of ultrasound transducers 60. For example, in illustrative FIG. 2 the array includes 32 transducers 60, and by way of illustration the blood flow velocity for the patch 16 may be determined as the average of the four highest determined transducer blood flow velocities of the set of 32 measured transducer blood flow velocities.

With continuing reference to FIGS. 2 and 3, it will be further recognized that this approach can be used to estimate the blood flow lumen. The transducer blood flow velocity for each ultrasound transducer of the array is determined as already described. The array defines an array area, and a map of the determined transducer blood flow velocities over the array area can be generated, as shown in FIG. 3. The blood flow lumen is then determined from the map of the determined transducer blood flow velocities over the array area. As shown in FIG. 3, this lumen may be taken as the lateral distance between the "edges" in the map where the flow velocities go from nearly zero to the maximum velocity. It will be appreciated that the resolution of the lumen estimation depends upon the spatial size of the transducers 60, with higher resolution being obtainable (possibly at some cost in noise) by using smaller transducer elements.

The ability to measure the blood flow lumen can be leveraged to assess flow mediated dilation (FMD). As is known in the medical arts, when flow is increased through a blood vessel, the size of the blood vessel can enlarge. This flow mediated dilation (FMD) reflects endothelial function. Diminished FMD can be indicative of sepsis. FMD can be monitored continuously using the approach described herein with reference to FIGS. 2 and 3, and FMD determined based on change in the determined blood flow lumen over time.

The illustrative ultrasound transducer patch 16 described with reference to FIGS. 2 and 3 has certain advantages. There is no need to laterally scan a formed ultrasound beam, which advantageously reduces hardware complexity. If the transducer array has sufficient lateral extent in the direction transverse to the longwise direction of the target blood vessel 64 (this vessel direction is usually known as basic human anatomy), then at least some transducers 60 of the array will be aligned with the targeted major blood vessel 64 when the patch is approximately placed on the vessel, thus relaxing the usual precision needed in positioning a handheld Doppler ultrasound transducer. This in turn means that the ultrasound transducer patch 16 can be placed and affixed (e.g. by gel or another adhesive) by medical personnel without particular ultrasound expertise (e.g., a nurse, rather than a specially trained diagnostic medical sonographer).

While the illustrative ultrasound transducer patch 16 described with reference to FIGS. 2 and 3 has certain advantages, it is contemplated to employ another type of ultrasound transducer patch in conjunction with the Doppler ultrasound instrument 10 of FIG. 1. For example, the transducer array of FIG. 2 can be replaced by a single ultrasound transducer for a given ultrasound patch. In such a case, the patch must be carefully aligned with the target blood vessel, for example by a trained sonographer employing audible flow velocity feedback to optimize the transducer position before affixing it to the hemodynamic measurement subject 22 by adhesive or so forth. In another contemplated embodiment, each ultrasound transducer patch includes an array of transducers designed to perform complex ultrasound beamforming and beam scanning in conjunction with beam steering electronics.

Figure 4:
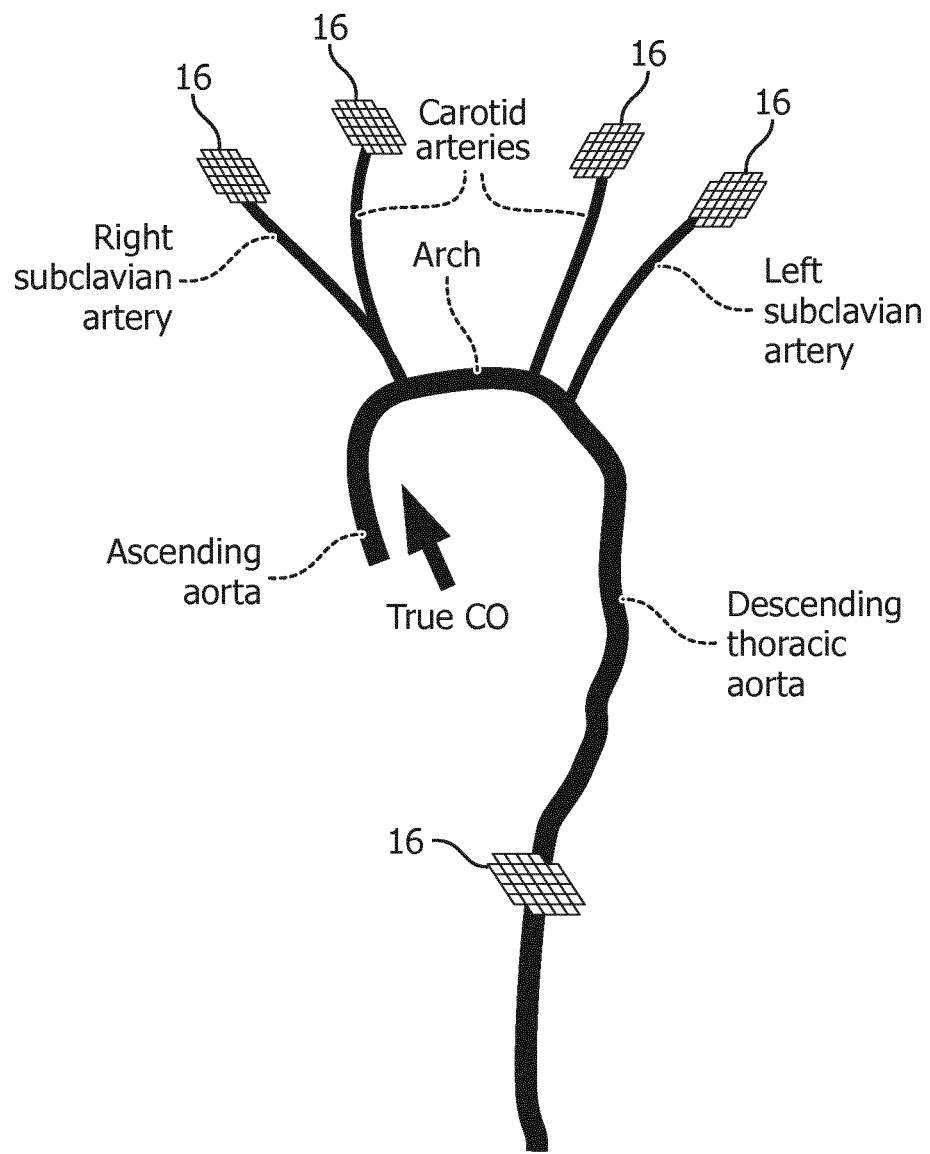
FIG. 4 diagrammatically illustrates an approach for non-invasively estimating cardiac output (CO) using the Doppler ultrasound device of FIG. 1.

With reference back to FIG. 1 and with further reference to FIG. 4, an illustrative example of an embodiment of the circulatory system-level processing 34 is described. This processing determines blood flow in a trunk blood vessel, namely the ascending aorta in illustrative FIG. 4, by combining measured blood flows in branching vessels connecting with the trunk blood vessel. The blood flow in the ascending aorta is delivered directly from the heart, and hence is equal to the cardiac output (CO), which is an important parameter in assessing cardiovascular health. In the illustrative example of FIG. 4, the branching blood vessels whose blood flow velocities are concurrently measured by ultrasound transducer patches 16 include the left and right carotid arteries which supply blood from the ascending aorta into the brain, the left and right subclavian arteries which supply blood to the left and right arms and some other upper regions, and the descending aorta which supplies blood to the legs and some other lower regions. As these five branching vessels are the major branches fed from the ascending aorta, the sum of blood flows in these five branching blood vessels should sum to equal the blood flow in the ascending aorta, i.e. the cardiac output (CO).

Doppler ultrasound provides the blood flow velocities in these five branching blood vessels monitored by the five patches 16 in the illustrative example of FIG. 4. To convert these blood velocities to blood flows (in units of volume/time), the velocity is suitably multiplied by the cross-sectional area of the blood flow lumen, which may be obtained experimentally using the approach described previously with reference to FIGS. 2 and 3. Denoting as $v_i$ the determined blood flow velocity corresponding to the $i^{th}$ ultrasound transducer patch, and denoting as $A_i$ the cross-sectional area of the blood flow lumen (i.e. blood vessel lumen) corresponding to the $i^{th}$ ultrasound transducer patch, the blood flow (in units of volume/time) for the branching blood vessel monitored by the $i^{th}$ ultrasound transducer patch is $v_i A_i$, and so the blood flow (in units of volume/time) for the trunk blood vessel is given by the sum:

$$\sum_{i=1}^{B} v_i A_i$$

where B denotes the total number of branches measured. The above equation assumes an average velocity, and may be adjusted for alternative flow models, e.g. using a parabolic velocity profile. In order for this measurement to be performed using the Doppler ultrasound instrument 10 of FIG. 1, B cannot be larger than N, i.e. the number of ultrasound transducer patches 16 that can be concurrently measured using the Doppler ultrasound instrument 10. It should be noted that while the cross-sectional areas $A_i$ can be obtained from the blood flow lumen measurements described with reference to FIGS. 2 and 3 (where $A_i = \pi r^2$ assuming a round cross-section and r is the blood flow radius, i.e. one-half of the measured diameter of the blood flow lumen), in other embodiments the cross-sectional areas $A_i$ may be obtained in other ways, such as using standard reference values.

Figure 5:
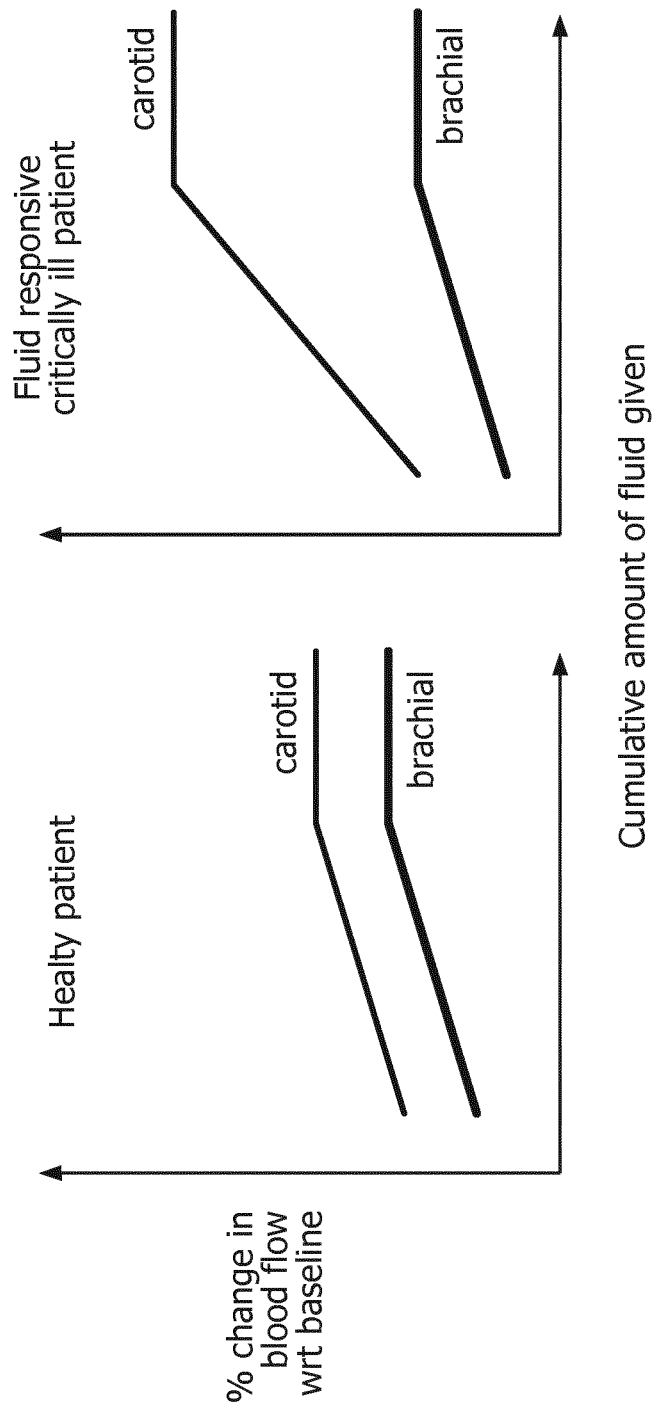
FIG. 5 diagrammatically illustrates fluid challenge data acquired for a carotid artery and a brachial artery in a single fluid challenge, with expected results shown for a healthy patient (left graph) and for a critically ill patient (right graph).

With reference back to FIG. 1 and with further reference to FIG. 5, another illustrative example of an embodiment of the circulatory system-level processing 34 is described. This processing simultaneously assesses hemodynamic response to a stimulus in K different blood vessels (where K is at least two and K is less than or equal to N in order for the measurement to be performed by the instrument 10). In the illustrative example, the stimulus is a fluid challenge. This response assessment is motivated by assessing whether fluid resuscitation is indicated. Fluid resuscitation is a common therapy given in critical care or surgical situations. However, studies have shown that only 50% of patients in critical care actually benefit from fluid resuscitation. Giving fluid to a patient who does not benefit from it is of no value and can actually lead to fluid overload which can cause increased morbidity and mortality. One way to assess fluid responsiveness is to measure the cardiac output before and after a fluid challenge procedure. If the cardiac output increases by 15% by the fluid challenge, then the patient is said to be fluid responsive. A responsive patient will often continue to receive fluid until he/she is no longer fluid responsive. The stimulus for a fluid challenge can be in the form of rapid administration of a small amount of fluid, or performing a passive leg raising test which then mobilizes the fluid in the legs to increase the blood that returns to the heart. Using the Doppler ultrasound instrument 10 of FIG. 1, blood flow velocity is measured as a function of time for K ultrasound transducer patches 16 operatively connected to the N channel connector port 14 from Doppler ultrasound data acquired using the respective ultrasound transducer patches 16. The hemodynamic response to the stimulus (e.g., fluid challenge) is determined for each of the K different blood vessels based on the K determined blood flow velocities as a function of time. FIG. 5 illustrates a schematic of a typical result, for monitoring of a carotid artery feeding the brain and a brachial artery feeding one arm. The left plot of FIG. 5 diagrammatically plots prophetic data for blood flow velocity in the carotid and brachial arteries for a healthy patient, while the right plot of FIG. 5 diagrammatically plots prophetic data for blood flow velocity in the carotid and brachial arteries for a critically ill patient. The inflection point in each plot where the curve transitions from a positive slope to a constant value indicates when the patient ceases to be fluid responsive. A significant difference between the healthy patient (left plot) and the critically ill patient (right plot) is that the latter exhibits preferential blood flow to the brain via the carotid artery in response to the fluid challenge. This reflects the expectation that, in critically ill patients, the body preferentially diverts flow to the brain rather than the rest of the body to protect cerebral blood flow, and represents a form of autoregulation. Monitoring of this differential flow can be useful for diagnosis as well as monitoring of therapy to check if flow to the brain is adequate. The differential in blood flow can be used to assess how sick a patient is, and how the patient is responding to resuscitation. Simultaneously measuring blood flow in the carotid artery and another artery supplying blood to the rest of the body (such as the illustrative brachial artery monitoring, and/or femoral artery monitoring), facilitates quantitative assessment of how the body is regulating blood to the brain versus the rest of the body. With the Doppler ultrasound instrument 10 of FIG. 1, flow can be tracked continuously to show when resuscitation has reached a plateau (see FIG. 5). The plateau is when more fluid will not be beneficial to a patient. Identifying when this plateau is reached is important because too much fluid resuscitation can increase patient mortality and morbidity.

Figure 6:
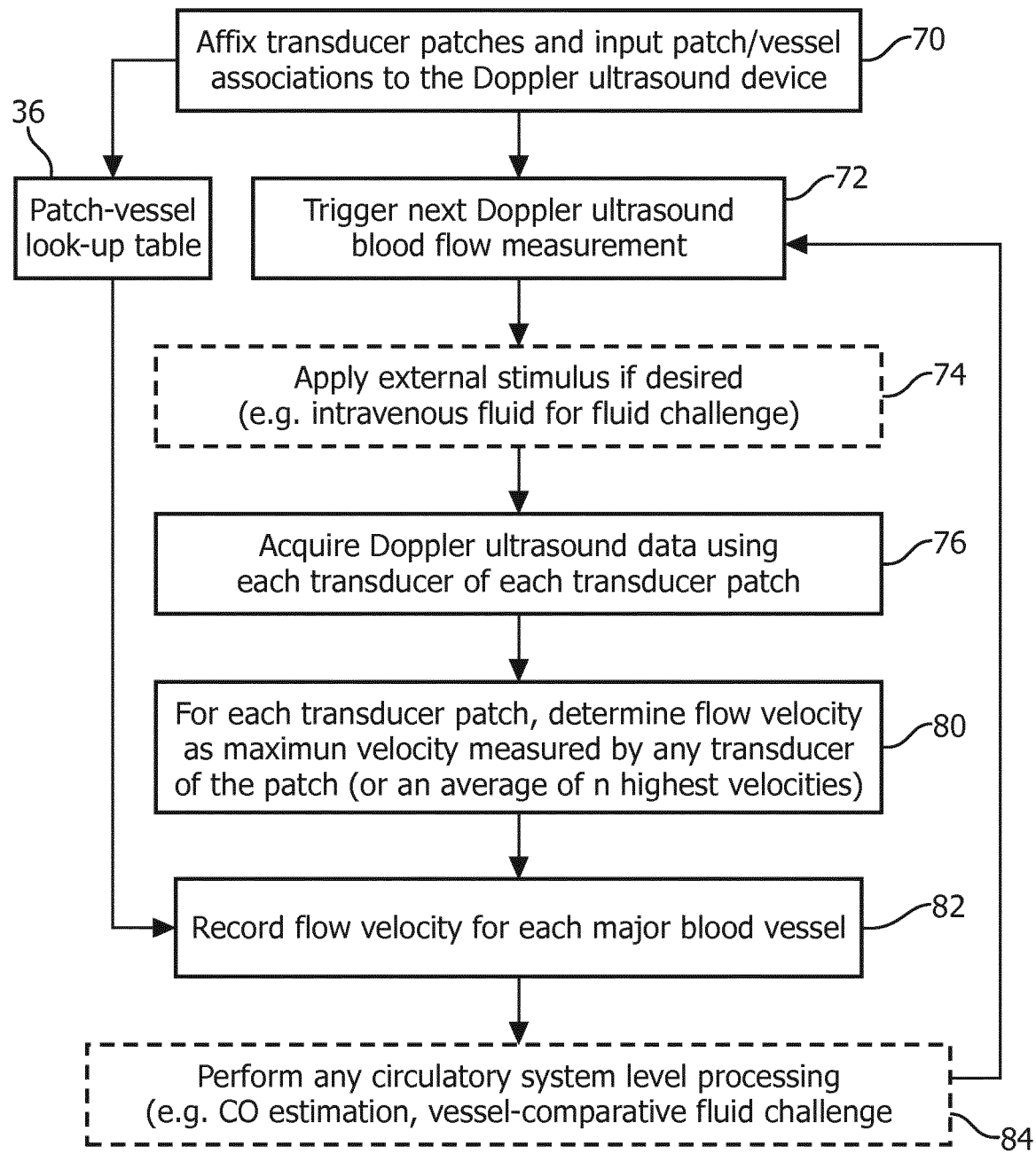
FIG. 6 diagrammatically illustrates a method of using the Doppler ultrasound device of FIG. 1 to perform automated blood velocity vital sign monitoring.

With continuing reference to FIG. 1 and with further reference now to FIG. 6, an illustrative Doppler ultrasound method is described, which monitors the subject 22 at regular intervals using the Doppler ultrasound instrument 10 of FIG. 1 and the illustrative ultrasound transducer patches 16 of FIG. 2. In an operation 70, the ultrasound transducer patches 16 are affixed to the subject 22, and the patch/vessel associations are inputted to the Doppler ultrasound instrument 10 via the user interface hardware 40 to create the patch-vessel look-up table 36. In an operation 72, a next Doppler ultrasound blood flow measurement is triggered, e.g. by the internal timer 46 or by an externally applied trigger signal. In an optional operation 74, a stimulus is applied (in the case of measuring hemodynamic response to a stimulus, e.g. as described with reference to FIG. 5). In an operation 76, Doppler ultrasound data are acquired using each transducer 60 of each transducer patch 16. The operation 76 may be performed in rapid succession for each patch 16 by cycling the MUX 26, or if multi-channel electronics are provided then the operation 76 may be performed simultaneously for all connected patches 16. In an operation 80 the patch level processing 32 is performed, e.g. by determining flow velocity as maximum velocity measured by any ultrasound transducer 60 of the ultrasound transducer patch 16 (or an average of n highest velocities). In an operation 82 the patch flow velocities are recorded, with reference to the look-up table 36, for each monitored major blood vessel. In an optional operation 84, selected circulatory system-level processing 34 is performed, for example determining a trunk vessel blood flow as described with reference to FIG. 4 and/or determining hemodynamic response to a fluid challenge (operation 74) as described with reference to FIG. 5. The Doppler ultrasound instrument 10 then goes into a waiting mode until the operation 72 triggers the next Doppler ultrasound blood flow measurement.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A Doppler ultrasound device comprising:
    a Doppler ultrasound instrument including:
        ultrasound pulse control and data acquisition electronics configured to acquire Doppler ultrasound data;
        an N-channel connector port configured to simultaneously operatively connect up to N ultrasound transducer patches with the ultrasound pulse control and data acquisition electronics where N is an integer equal to or greater than two, wherein each ultrasound transducer patch includes an ultrasound transducer array comprising ultrasound transducers; and
        an electronic processor programmed to concurrently determine up to N blood flow velocities corresponding to up to N ultrasound transducer patches operatively connected to the N-channel connector port from Doppler ultrasound data acquired using the respective ultrasound transducer patches,
        wherein the electronic processor is further programmed to determine the blood flow velocity for each ultrasound transducer patch by operations including:
            determining a transducer blood flow velocity for each ultrasound transducer of an array of ultrasound transducers of the ultrasound transducer patch from Doppler ultrasound data acquired using the ultrasound transducer; and
            determining the blood flow velocity for the ultrasound transducer patch as a highest determined transducer blood flow velocity of the array of ultrasound transducers or as an aggregation of a set of highest determined transducer blood flow velocities of the array of ultrasound transducers;

wherein the electronic processor of the Doppler ultrasound instrument is further programmed to determine a blood flow lumen by operations including:

mapping the array of ultrasound transducers of the ultrasound transducer patch that define an array area; and determining the blood flow lumen from a map of the determined transducer blood flow velocities over the array area;

wherein the electronic processor of the Doppler ultrasound instrument is further programmed to determine flow mediated dilation (FMD) based on change in the determined blood flow lumen over time.

2. The Doppler ultrasound device of claim 1 wherein the ultrasound pulse control and data acquisition electronics includes one of:

(1) a multiplexor switchable to sequentially connect the ultrasound pulse control and data acquisition electronics with each channel of the N-channel connector port; and (2) N electronics channels each connecting with a corresponding channel of the N-channel connector port.

3. The Doppler ultrasound device of claim 1 wherein the N-channel connector port includes one of:

(1) N connectors each configured to connect with a single ultrasound transducer patch; and (2) one connector configured to connect with an N-to-1 pigtail connector of a bundle of N ultrasound transducer patches.

4. The Doppler ultrasound device of claim 1 wherein the electronic processor of the Doppler ultrasound instrument is further programmed to determine a blood flow in a trunk blood vessel connecting with B branch blood vessels where B is at least two and B is less than or equal to N by operations including:

determining B blood flow velocities corresponding to B ultrasound transducer patches operatively connected to the N-channel connector port from Doppler ultrasound data acquired using the respective ultrasound transducer patches; and computing the blood flow in the trunk blood vessel using the determined B blood flow velocities and blood vessel lumens for the B branch blood vessels.

5. The Doppler ultrasound device of claim 1 wherein the electronic processor of the Doppler ultrasound instrument is further programmed to simultaneously assess hemodynamic response to a stimulus in K different blood vessels where K is at least two and K is less than or equal to N by operations including:

determining blood flow velocity as a function of time for K ultrasound transducer patches operatively connected to the N-channel connector port from Doppler ultrasound data acquired using the respective ultrasound transducer patches; and determining the hemodynamic response to the stimulus for each of the K different blood vessels based on the K determined blood flow velocities as a function of time.

6. The Doppler ultrasound device of claim 1 further comprising:

N ultrasound transducer patches, each connectable to the N-channel connector port of the Doppler ultrasound instrument to operatively connect with the ultrasound pulse control and data acquisition electronics simultaneously with up to N−1 of the other N ultrasound transducer patches.

7. The Doppler ultrasound device of claim 1 further comprising:

between two and N ultrasound transducer patches simultaneously connected to the N-channel connector port of the Doppler ultrasound instrument and thereby simultaneously operatively connected with the ultrasound pulse control and data acquisition electronics.

8. The Doppler ultrasound device of claim 6 wherein each ultrasound transducer patch includes an adhesive by which the ultrasound transducer patch is operatively connectable to skin of a hemodynamic measurement subject.

9. A Doppler ultrasound method comprising:

affixing two or more ultrasound transducer patches, wherein each ultrasound transducer patch includes an ultrasound transducer array comprising ultrasound transducers, to different locations on a hemodynamic measurement subject;

concurrently acquiring Doppler ultrasound data using the two or more ultrasound transducer patches affixed to the different locations on the hemodynamic measurement subject; and determining a blood flow velocity for each location using the Doppler ultrasound data acquired using the ultrasound transducer patch affixed to the location, wherein the blood flow velocity is determined for each location by operations including:

determining a transducer blood flow velocity for each ultrasound transducer of each array of ultrasound transducers using Doppler ultrasound data acquired using the ultrasound transducer; and determining the blood flow velocity for the ultrasound transducer patch as a highest determined transducer blood flow velocity of the array of ultrasound transducers or as an aggregation of a set of highest determined transducer blood flow velocities of the array of ultrasound transducers; and mapping the array of ultrasound transducers of the ultrasound transducer patch that define an array area; and determining a blood flow lumen from a map of the determined transducer blood flow velocities over the array area; and determining flow mediated dilation (FMD) based on change in the determined blood flow lumen over time.

10. The Doppler ultrasound method of claim 9 wherein the plurality of different locations on the hemodynamic measurement subject align with locations of branching blood vessels that connect with a trunk blood vessel and the method further comprises:

determining blood flows in the branching blood vessels from the blood flow velocities determined for the different locations on the hemodynamic measurement subject; and computing a blood flow in the trunk blood vessel by adding together the determined blood flows in the branching blood vessels.

11. The Doppler ultrasound method of claim 9 further comprising:

applying a stimulus to the hemodynamic measurement subject;

determining the blood flow velocities for the different locations on the hemodynamic measurement subject as a function of time at least after applying the stimulus; and determining a hemodynamic response to the stimulus for each of a plurality of different blood vessels based on the blood flow velocities as a function of time at the different locations on the hemodynamic measurement subject.

12. The Doppler ultrasound method of claim 11 wherein the stimulus is a fluid challenge.

13. The Doppler ultrasound method of claim 9 further comprising:
   automatically repeating the concurrent acquiring and the determining at a programmed automatic repetition time interval; and
   plotting a trend line for each determined blood flow velocity as a function of time.

\* \* \* \* \*